United States Patent [19]
Bates et al.

[11] 4,094,879
[45] June 13, 1978

[54] PRODUCTION OF 5-NITROTETRAZOLE SALTS

[75] Inventors: Leslie Raymond Bates, Cheshunt; John Michael Jenkins, Sevenoaks, both of England

[73] Assignee: The Secretary of State for Defence in Her Britannic Majesty's Government of the United Kingdom of Great Britain and Northern Ireland, London, England

[21] Appl. No.: 737,692

[22] Filed: Nov. 1, 1976

[30] Foreign Application Priority Data

Nov. 11, 1975 United Kingdom ............... 46605/75

[51] Int. Cl.$^2$ .......................... C07F 3/14; C07F 1/10; C07F 1/08
[52] U.S. Cl. .................................................. 260/299
[58] Field of Search ......................................... 260/299

[56] References Cited
U.S. PATENT DOCUMENTS 2,066,954  1/1937  von Herz .............................. 260/299

OTHER PUBLICATIONS

Taylor et al, Symp. Chem. Probl. Connected Stab. Explosive [Proc.]3rd 1973 (Pub. 1974) 43-46.

Primary Examiner—Donald G. Daus
Assistant Examiner—Diana G. Rivers
Attorney, Agent, or Firm—Stevens, Davis, Miller & Mosher

[57] ABSTRACT

Silver and mercury 5-nitrotetrazole salts are prepared by forming an acid solution of a complex of cupric 5-nitrotetrazole with an aliphatic chelating amine and adding to the acid solution a solution of a soluble silver or mercury salt. The silver or mercury 5-nitrotetrazole salt is precipitated and filtered off. The cupric 5-nitrotetrazole amine complex may first be decomposed by reacting with a mixture of nitric acid and a nitrite and the silver or mercury salt solution then added to precipitate the corresponding 5-nitrotetrazole salt. The silver and mercury nitrotetrazole salts are useful as explosives.

20 Claims, No Drawings

PRODUCTION OF 5-NITROTETRAZOLE SALTS

This invention relates to the production of heavy metal salts of 5-nitrotetrazole for use as initiating explosives.

U.S. Pat. No. 2,066,954 describes the production of silver and mercuric 5-nitrotetrazoles via simultaneous diazotisation/nitration reaction of 5-aminotetrazole in the presence of copper salts to give the acid copper salt formulated $Cu(NT)_2$ NTH $4H_2O$ ($NT$ = 5-nitrotetrazole anion). This was converted to the required heavy metal salt via either the sodium salt $[Na(NT)]xH_2O$ or the free acid (HNT). Subsequently preparation of silver and mercuric 5-nitrotetrazoles direct from the acid salt has been described.

Intermediate salts in the preparation of initiating explosives should be stable, safe to handle and easy to prepare with reproducible composition and low impurity level to facilitate control of the composition and impurity level of the final initiating explosive. All the above 5-nitrotetrazole intermediates are unsatisfactory in at least one of these respects; the sodium salt has high solubility making it difficult and expensive to isolate and purify and shows a variable level of hydration from $x = 4$ to $x = 1$; the acid copper salt forms as a gelatinous material which is difficult to filter and wash free of ionic impurities and dries to a fluffy powder which is difficult to handle and of variable composition; the free acid is very hygroscopic and is liable to explode spontaneously under ambient conditions making it totally unsuitable as a manufacturing intermediate. Other metal salts (for example barium and thallium) have been found unsuitable as intermediates due to excessive hydration or high solubility.

A more satisfactory intermediate salt for use in the production of heavy metal salts of 5-nitrotetrazole is provided by a complex of cupric 5-nitrotetrazole with an aliphatic chelating amine. Preferably the aliphatic chelating amine is one which will not alter the valency of the cupric ion, for example a diamine such as ethylene diamine or 1,3-diaminopropane.

These amine complexes of cupric 5-nitrotetrazole have been prepared via the sodium nitrotetrazole salt. However due to the aforementioned disadvantages of this latter material as an intermediate, an improved method of preparing the amine complexes has been sought which avoids or minimises the involvement of unsatisfactory intermediates. This invention is concerned with the preparation of the amine complexes and with their conversion to silver and mercury 5-nitrotetrazoles.

Accordingly the present invention provides a method of preparing a silver or mercury 5-nitrotetrazole which comprises forming an acid solution of a complex of cupric 5-nitrotetrazole with an aliphatic chelating amine, adding to said acid solution at a temperature of at least 50° C, a solution of a soluble silver or mercury salt to precipitate the required 5-nitrotetrazole salt, and filtering off the 5-nitrotetrazole salt.

Optionally the amine complex may be decomposed before addition of the solution of the soluble silver or mercury salt by the addition thereto of nitric acid and a nitrite followed by heating to expel the nitrogen and nitrogen oxides formed and leave a solution of the free copper 5-nitrotetrazole salt. This solution is then reacted with the soluble silver or mercury salt solution to give the silver or mercury 5-nitrotetrazole.

The silver and mercuric salts are known to be useful primary explosives and it has also been found that the mercurous salt is potentially useful.

Conveniently, the amine complex of cupric 5-nitrotetrazole is prepared by adding to a slurry of acid copper 5-nitrotetrazole maintained at a temperature of at least 40° C in a slurrying medium, a copper salt which is soluble in the slurrying medium, and an aliphatic chelating amine, stirring the mixture to dissolve the acid salt and thereafter cooling the mixture to precipitate the required amine complex of cupric 5-nitrotetrazole. The product is obtained in good yield and with reproducible impurity levels. It is stable under ambient conditions and is reasonably safe and easy to handle.

In the method of preparing the silver and mercury salts by direct treatment of the amine complex with the silver or mercury salt solution, the acid solution of the complex salt is preferably formed at an elevated temperature e.g. at least 50° C and typically 70° C, in order to dissolve a satisfactory amount of the complex salt. If it is attempted to carry out the reaction at lower temperatures, undissolved particles may be present, and these will act as nuclei for the silver or mercury nitrotetrazole when the salt is precipitated and will form an impurity in the final product. The acid solution of the complex salt preferably contains an acid at a concentration of at least 3, most preferably 4 to 5, equivalents per mole of complex salt. Nitric acid is preferably used as the acid. The concentration of the complex will depend on the temperature of the reaction, but should normally be within the range 20 to 100g/liter. The solutions are normally aqueous solutions.

In the case where the complex is first decomposed, the reaction with nitrite and nitric acid should be carried out at about ambient temperature or slightly above, after which the mixture should be heated to at least 80° C and normally about 90°–100° C to remove the gaseous products and dissolve the free copper salt. The nitrite used is typically an alkali metal nitrite, for example sodium nitrite.

The soluble silver or mercury salt should in either case normally be added dropwise as an aqueous solution, typically having a strength of about 0.5 to 2N, to the copper 5-nitrotetrazole solution and for maximum purity in the product the addition should take place at a temperature within the range 55°–95° C. The silver or mercury salt may conveniently be the nitrate. The mixture is stirred to complete the reaction and filtered hot or after cooling.

The amine complex of cupric 5-nitrotetrazole is generally prepared using an aqueous slurry, and, as the soluble copper salt, copper sulphate is conveniently used. The slurry should generally be maintained at a temperature below 95° C if in water, and most preferably is kept at 70° C.

Mercuric 5-nitrotetrazole prepared by the process of the invention has a higher bulk density than the salt prepared by other routes, making it especially suitable for automatic filling of small detonators. According to yet another aspect of the invention, therefore, there is provided mercuric 5-nitrotetrazole in the form of a powder having a bulk density of at least 1.1 g/ml (measured after gravitational settling of a known weight in butyl alcohol).

Various materials and processes in accordance with the invention will now be specifically described by way of example. All temperatures are in ° C.

EXAMPLE 1

Preparation of Bis (ethylenediamino) Copper II 5-nitrotetrazolate 1178 g. of an aqueous slurry of acid copper 5-nitrotetrazole [Cu(NT)$_2$HNT 4 H$_2$O] containing 378 g of the salt was placed in a 10 liter stainless steel pan with 1,200 ml of water and stirred till homogenous. The temperature was raised to 70°.

A mixture of 98.5 g copper sulphate pentahydrate, 166 g ethylene diamine and 400 mls water was added in a stream. Stirring was continued until all the Cu(NT)$_2$HNT 4H$_2$O was dissolved. The solution was then cooled to 17° over a period of 30 minutes.

The Cu(en)$_2$NT$_2$ is filtered off and washed with cold water and dried. Yield = 380 g.

EXAMPLE 2

Preparation of Bis(1,3diaminopropane) Copper II 5-nitrotetrazolate 39g of an aqueous slurry of acid copper 5-nitrotetrazole containing 24 g of the salt was stirred with 100 mls of water at 50°.

A mixture of 5g copper acetate monohydrate 13g propylenediamine and 10 mls water was added in a stream. Stirring was continued until all the Cu (NT)$_2$ HNT 4H$_2$O was dissolved. The solution was then cooled to 20° over a period of 15 minutes.

The [Cu(pn)$_2$]NT$_2$ was filtered off, washed with cold water and dried. Yield = 27g.

EXAMPLE 3

Preparation of Mercuric 5-nitrotetrazole 20.55 g [Cu(en)$_2$] NT$_2$ was dissolved in 235 mls water at 70°. 42 mls of 5N nitric acid was added drop wise over 10 mins. The solution was cooled to 55° and a solution of mercuric nitrate (17.5 g in 90 mls water + 5 mls 5N nitric acid) was added drop wise over 40 minutes. The solution was stirred for a further 10 minutes then filtered, and the precipitate was washed with cold water and dried. Yield = 19g Hg(NT)$_2$. Bulk density = 1.25 g/ml.

EXAMPLE 4

Alternative route to Mercuric 5-nitrotetrazole 10 g [Cu(en)$_2$] NT$_2$ was stirred with a solution of 6.8g sodium nitrite in 100 mls water at 24°. 50 mls of 2.5N nitric acid was added drop wise over 15 minutes and the solution was stirred for a further 10 minutes. The solution was then heated, with steam, to 95° for 10 minutes to expel all nitrogen and nitrogen oxide. The solution was cooled to 55° and a solution of mercuric nitrate (10 g in 30 mls water + 3 mls 5N nitric acid) was added drop wise over 15 mins. The solution was stirred for a further 10 minutes then filtered and the precipitate was washed with cold water and dried. Yield = 8.5 g. Bulk density = 1.21 g/ml.

EXAMPLE 5

Preparation of Silver 5-Nitrotetrazole 10 g [Cu(en)$_2$] NT$_2$ was stirred with a solution of 6.8 g of sodium nitrite in 100 mls of water at 25°. 50 mls of 2.5N nitric acid was added drop wise over 15 minutes and the solution stirred for a further 15 minutes. The solution was then heated, with steam, to 95° for 10 minutes to expel all nitrogen and nitrogen oxides. The solution was cooled to 60° and a solution of silver nitrate (8.3 g in 50 mls water) was added dropwise over 15 minutes. The solution was stirred for a further 10 minutes then filtered and the precipitate washed with cold water and dried. Yield = 10.5 g AgNT

EXAMPLE 6

Preparation of Mercurous 5-Nitrotetrazole 16.44g [Cu(en)$_2$]NT$_2$ was dissolved in 190mls water at 70°. 34mls of 5N nitric acid was added dropwise over 10 mins. The solution was cooled to 60° and a solution of mercurous nitrate (22.44g in 95 mls of water + 5 N nitric acid) was added dropwise over 30 minutes. The solution was stirred for a further 10 minutes then filtered and the precipitate washed with cold water and dried. Yield = 18g Hg$_2$ NT$_2$.

We claim:

1. A method of preparing a silver or mercury 5-nitrotetrazole, which comprises forming an acid solution of a complex of cupric 5-nitrotetrazole with an aliphatic chelating amine, adding to said acid solution at a temperature of at least 50° C, a solution of a soluble silver or mercury salt to precipitate the required 5-nitrotetrazole salt, and filtering off the 5-nitrotetrazole salt.

2. A method according to claim 1, wherein, before the addition of the soluble silver or mercury salt, the amine complex of cupric 5-nitrotetrazole is decomposed by the addition of nitric acid and a nitrite followed by heating to expel the nitrogen and nitrogen oxides produced and leave a solution of the free copper 5-nitrotetrazole salt.

3. A method according to claim 1, wherein the acid solution of the complex salt is formed at a temperature of at least 50° C and wherein the acid is present at a concentration of at least 3 equivalents per mole of the complex salt.

4. A method according to claim 3, wherein the temperature is around 70° C.

5. A method according to claim 3, wherein the acid is present at a concentration of from 4 to 5 equivalents per mole of complex salt.

6. A method according to claim 3, wherein the acid is nitric acid.

7. A method according to claim 3, wherein the complex salt is present at a concentration of from 20 to 100g/liter.

8. A method according to claim 2, wherein the complex salt is reacted with the nitrite and nitric acid at or slightly above ambient temperature.

9. A method according to claim 2, wherein the nitrite is sodium nitrite,

10. A method according to claim 2, wherein the solution is heated to at least 80° C to expel the nitrogen and nitrogen oxides produced.

11. A method according to claim 10, wherein the solution is heated to a temperature of from 90° to 100° C.

12. A method according to claim 1, wherein the solutions are aqueous solutions.

13. A method according to claim 1, wherein the aliphatic chelating amine is ethylene diamine or 1,3-diaminopropane.

14. A method according to claim 1, wherein the solution of the soluble silver or mercury salt is added to the copper 5-nitrotetrazole solution at a temperature of from 55° to 95° C.

15. A method according to claim 1, wherein the soluble silver or mercury salt is silver nitrate or mercuric or mercurous nitrate.

16. A method according to claim 1, wherein the amine complex of cupric 5-nitrotetrazole is prepared by adding to a slurry of acid copper 5-nitrotetrazole maintained at a temperature of at least 40° C in a slurrying medium, a copper salt which is soluble in said slurrying medium and an aliphatic chelating amine, stirring the mixture and thereafter cooling the mixture to precipitate the required amine complex of cupric 5-nitrotetrazole, and recovering the amine complex.

17. A method according to claim 16, wherein the slurrying medium is water.

18. A method according to claim 16, wherein the soluble copper salt is copper sulphate.

19. A method according to claim 16, wherein the slurry is maintained at a temperature below 95° C.

20. A method according to claim 19, wherein the slurry is maintained at around 70° C.